(12) United States Patent
Flexman et al.

(10) Patent No.: US 10,994,095 B2
(45) Date of Patent: May 4, 2021

(54) HUB FOR DEVICE PLACEMENT WITH OPTICAL SHAPE SENSED GUIDEWIRE

(71) Applicant: KONINKLIJKE PHILIPS N.V., Eindhoven (NL)

(72) Inventors: Molly Lara Flexman, Melrose, MA (US); Sander Hans Denissen, Best (NL); David Paul Noonan, New York, NY (US); Neriman Nicoletta Kahya, Eindhoven (NL); Aryeh Leib Reinstein, Bronx, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 254 days.

(21) Appl. No.: 15/761,902

(22) PCT Filed: Sep. 8, 2016

(86) PCT No.: PCT/IB2016/055341
§ 371 (c)(1),
(2) Date: Mar. 21, 2018

(87) PCT Pub. No.: WO2017/055950
PCT Pub. Date: Apr. 6, 2017

(65) Prior Publication Data
US 2018/0264227 A1    Sep. 20, 2018

Related U.S. Application Data

(60) Provisional application No. 62/236,180, filed on Oct. 2, 2015.

(51) Int. Cl.
*A61M 25/00* (2006.01)
*A61B 34/20* (2016.01)
(Continued)

(52) U.S. Cl.
CPC ......... *A61M 25/0097* (2013.01); *A61B 5/065* (2013.01); *A61B 34/20* (2016.02);
(Continued)

(58) Field of Classification Search
CPC ........ A61M 25/0097; A61M 25/09041; A61M 2025/0166; A61B 34/20; A61B 5/065;
(Continued)

(56) References Cited

U.S. PATENT DOCUMENTS 6,053,913 A    4/2000    Tu et al.
8,728,097 B1   5/2014    Sugimoto et al.
(Continued)

FOREIGN PATENT DOCUMENTS

WO    2011059889 A1    5/2011
WO    2012029013 A1    3/2012
(Continued)

*Primary Examiner* — Katrina M Stransky

(57) ABSTRACT

A system for deploying a device includes an elongated flexible instrument (108) and a shape sensing system (104) coupled to the flexible instrument. A hub (106) includes a shape profile configured to receive and maintain the flexible instrument with the shape sensing system therein. The shape profile includes a shape to track a position or a rotation of the hub relative to a reference position using the shape sensing system. The hub is configured to be coupled to a deployable device (102) such that a change in the position or rotation of the hub indicates a corresponding change in the deployable device.

19 Claims, 9 Drawing Sheets

(51) Int. Cl.
*A61M 25/09* (2006.01)
*A61M 25/10* (2013.01)
*A61B 90/90* (2016.01)
*A61M 25/01* (2006.01)
*A61B 5/06* (2006.01)
*A61F 2/07* (2013.01)
*A61F 2/95* (2013.01)

(52) U.S. Cl.
CPC .................. *A61F 2/07* (2013.01); *A61F 2/95* (2013.01); *A61M 25/09041* (2013.01); *A61M 25/10* (2013.01); *A61B 5/066* (2013.01); *A61B 90/90* (2016.02); *A61B 2034/2051* (2016.02); *A61B 2034/2061* (2016.02); *A61M 25/0108* (2013.01); *A61M 2025/0166* (2013.01); *A61M 2205/3306* (2013.01); *A61M 2205/502* (2013.01)

(58) Field of Classification Search
CPC ............ A61B 5/066; A61B 2034/2061; A61B 2034/2051
See application file for complete search history.

(56) References Cited

U.S. PATENT DOCUMENTS

| | | |
|---|---|---|
| 2008/0140180 A1 | 6/2008 | Dolan et al. |
| 2011/0087112 A1* | 4/2011 | Leo ..................... A61B 5/6885 600/478 |
| 2011/0118749 A1* | 5/2011 | Prisco ................... A61B 34/70 606/130 |
| 2011/0202069 A1* | 8/2011 | Prisco ................... A61B 34/30 606/130 |
| 2014/0277091 A1 | 9/2014 | Breedlove |
| 2015/0142013 A1 | 5/2015 | Tanner et al. |

FOREIGN PATENT DOCUMENTS

| | | |
|---|---|---|
| WO | 2012109760 A1 | 8/2012 |
| WO | 2014089273 A1 | 6/2014 |
| WO | 2015049142 A1 | 4/2015 |
| WO | 2015049612 A2 | 4/2015 |

* cited by examiner

HUB FOR DEVICE PLACEMENT WITH OPTICAL SHAPE SENSED GUIDEWIRE

CROSS-REFERENCE TO PRIOR APPLICATIONS

This application is the U.S. National Phase application under 35 U.S.C. § 371 of International Application Serial No. PCT/IB2016/055341, filed on Sep. 8, 2016, which claims the benefit of U.S. Patent Application No. 62/236, 180, filed on Oct. 2, 2015. This application is hereby incorporated by reference herein.

BACKGROUND

Technical Field

This disclosure relates to medical instruments and more particularly to shape sensing optical fibers in guidewires configured to sense over-the wire components in medical applications.

Description of the Related Art

A medical device such as a catheter, deployment system, or sheath can be enabled with shape sensing by embedding an optical fiber(s) within the device. This requires customizing a mechanical design of the device to add an additional lumen for the fiber. Adding the fiber also adds cost to the device and necessitates the use of an additional shape sensing system. Such devices are known as 'over-the-wire' devices as they are typically used in conjunction with a guidewire that travels through a lumen in the device.

Optical shape sensing (OSS) or Fiber-Optical RealShape™ (also known as "Optical Shape Sensing", "Fiber Shape Sensing", "Fiber Optical 3D Shape Sensing", "Fiber Optic Shape Sensing and Localization" or the like) employs light along a multicore optical fiber for device localization and navigation during surgical intervention. One principle involved makes use of distributed strain measurement in the optical fiber using characteristic Rayleigh backscatter or controlled grating patterns. Multiple optical fibers can be used together to reconstruct a 3D shape, or a single optical fiber with multiple cores that may also be helixed for a lower-profile sensor. The shape along the optical fiber begins at a specific point along the sensor, known as the launch or z=0, and the subsequent shape position and orientation are relative to that point. Optical shape sensing fibers can be integrated into medical devices to provide live guidance of the devices during minimally invasive procedures.

In the event that shape sensing is to be used for positioning and orienting a device with a guidewire that travels through a lumen in the device, it is necessary to have rotational information. However, the guidewire and over-the-wire device are not rotationally coupled within the body. As a result, the problem of determining the orientation of the over-the-wire device is not addressed.

SUMMARY

In accordance with the present principles, a system for deploying a device includes an elongated flexible instrument and a shape sensing system coupled to the flexible instrument. A hub includes a shape profile configured to receive and maintain the flexible instrument with the shape sensing system therein. The shape profile includes a shape to track a position or a rotation of the hub relative to a reference position using the shape sensing system. The hub is configured to be coupled to a deployable device such that a change in the position or rotation of the hub indicates a corresponding change in the deployable device.

Another system for deploying a device includes a shape sense enabled guidewire and a hub including a profile configured to receive and maintain the shape sense enabled guidewire therein. The profile includes a shape to permit identification of at least one of a position or a rotation of the hub relative to a reference position using shape sensing. An over-the-wire device is connectable to the hub during deployment. A registration module registers anatomical images with the hub to infer a position or rotation of the device in accordance with the at least one of position or rotation of the hub.

A method for deploying a device includes attaching a hub on an elongated flexible instrument having a shape sensing system coupled to the flexible instrument, the hub including a shape profile configured to receive and maintain the flexible instrument with the shape sensing system therein; registering a target feature on a deployed instrument to the hub; displaying a representation of the deployed instrument on an image using at least one of a position or a rotation of the hub provided by the shape sensing system relative to the image where a change in the at least one of position or rotation of the hub indicates a corresponding change in the deployed instrument; and refining the at least one of position or rotation of the representation in the image.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
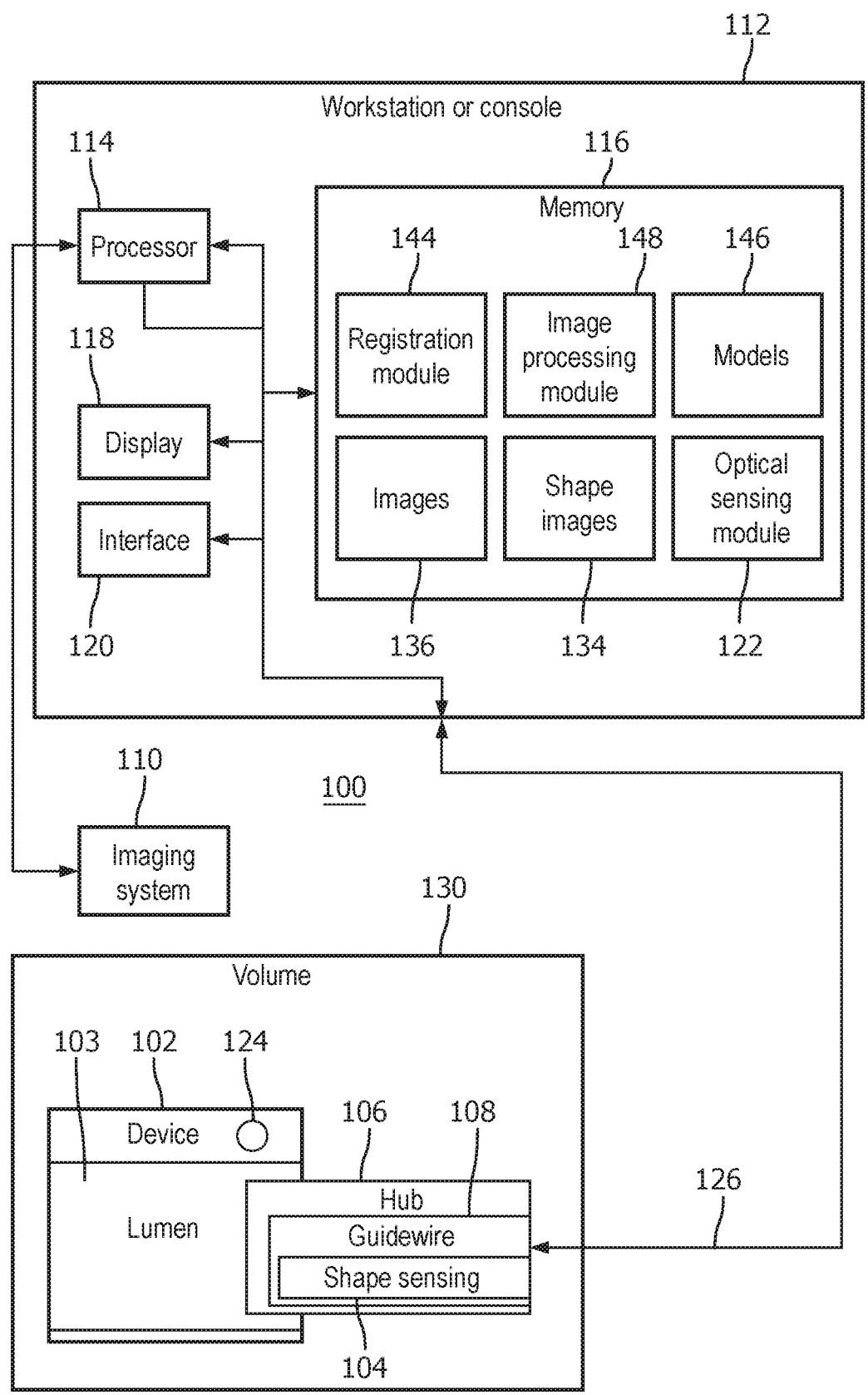
FIG. 1 is a block/flow diagram showing a shape sensing hub for inferring a position/orientation of a deployable device in accordance with one embodiment.

In accordance with the present principles, a shape sensed guidewire is provided for use in a lumen that also senses the position of any commercial over-the-wire device or component. If a catheter (or other deployable device) is employed over a shape sensed guidewire (or other flexible elongated device) then the guidewire shape also defines the catheter shape for the length over which the catheter overlaps the guidewire. To properly define the position of the catheter, a relationship between the catheter and the guidewire needs to be known. This can be done by using a hub device to cause the guidewire to take on a specific shape, curvature, or strain profile (shape profile) at a specific position along the catheter. A method to induce such a shape, curvature or strain profile is to employ the 'hub' with a known profile which can be stored as a template.

When a shape sensed device is inside a non-shape sensed device, the shape information from the sensed device can be used to infer information about the shape and position of the unsensed device. The registration needed may include a longitudinal translation between the two devices. This registration can be performed by using a known shape deformation of the sensed device at a specific location along the unsensed device. The shape deformation can be detected through curvature detection, axial strain (from heating or tensions), 2D or 3D shape matching, etc.

Multiple different versions of hub designs may be employed. In the case of hubs that use a shape deformation (as opposed to a strain deformation due to temperature, for example), the shape deformation will also define a plane. The same hub device can be used to track orientation of the device (e.g., roll about its longitudinal axis). Orientation of the hub in a proximal part of the device may map 1-to-1 to a therapeutic such as a balloon, valve, endograft, stent, etc. located in the distal portion.

A hub may be defined as a component that can create a shape or curvature deformation in a shape sensed device, such as a guidewire. Such a component should be able to work in a wide range of commercially available medical devices within a clinical environment. The hub design can be employed across multiple device designs. Multiple different versions of hub designs can be used for deforming the guidewire and performing longitudinal encoding.

Once the position and orientation of the over-the-wire device is known, it can be used to display a model of a therapeutic such as a balloon, valve, endograft, stent, etc. In endovascular aneurysm repair (EVAR), the position of the endograft needs to be known so that other catheters and endografts can be navigated with respect to an original endograft. This calls for significant amounts of fluoroscopy and contrast. If the endografts are not correctly positioned, a number of issues may arise.

EVAR replaced open surgery as the most common technique for the repair of abdominal aortic aneurysms (AAA). The procedure is usually carried out under x-ray fluoroscopy guidance and uses significant amounts of contrast to position and deploy the stent graft correctly. On average 50-100 mL of contrast dye is used during an EVAR procedure, which can result in acute renal failure in ~7% of cases. One complication from EVAR is endoleaks resulting from an insufficient seal of the stent graft to the aorta. Endoleaks involve incorrect flow around the stent (for example, flow around the stent at the proximal or distal attachment site, flow through the graft wall, retrograde flow from the branches, etc.). Another complication around EVAR involves ischemia of the aortic side branches (such as the colonic, renal, and pelvic arteries). This can occur due to misplacement of the stent graft such that the stent partially or completely covers one of the side vessels, and this is associated with a lack of high-quality imaging technology as well as the learning curve of the endovascular team.

In EVAR, stent grafts are contained within a stent-deployment system that is employed to navigate the stent to the correct part of the vasculature. The deployment systems tend to be relatively large and stiff endovascular devices. They typically involve a handle or set of knobs and dials at the proximal end to control the various steps around the stent deployment. The stent lies within the distal part of the device and is only released once the device has been navigated to the appropriate location. In some cases the stent completely deploys in one step, while in other cases the stent can be partially deployed to allow for correct positioning and orientation before the final deployment step firmly attaches the stent to the vasculature (typically through the retaining/sealing ring).

The endovascular stent graft needs a sufficient amount of healthy vasculature where it can land its sealing ring. If this is not possible beneath the renal arteries, then the stent will cover those arteries, and needs to create some alternative way of maintaining flow to those vessels. This can be done with a fenestrated stent (e.g., a stent with windows for the side-branches) in a procedure known as fenestrated endovascular aneurysm repair (FEVAR). In this case the stent has fenestrations that are lined up correctly with the side branches and additional stents are placed to connect the side vessels to the main stent.

Under x-ray guidance the stent can be visualized through x-ray visible markers that are located in key positions on the stent. In the fenestrated stent, the markers identify the locations of the fenestrations and can be used to orient the stent to appropriately align the fenestrations with the side vessels.

In accordance with the present principles, devices and methods include registering a hub to a target node of an over-the-wire device and visualizing the over-the-wire device and a model at a target node in the over-the-wire device. This permits any commercial catheter, deployment system, sheath, or other such device to be navigated using a shape sensed guidewire. In useful embodiments, devices and methods make use of a proximal hub to determine orientation of a distal portion of a device such as a commercially available catheter, deployment system, or sheath that is fitted over a shape sensing guidewire. The hub may include a shape profile that deflects the guidewire passing through it into a known shape. That shape can be detected along the fiber to know the longitudinal registration between the guidewire and the over-the-wire device. Since the hub is coupled to the over-the-wire device, the hub shape can also be used to track the rotation applied to the proximal part of the over-the-wire device.

In one embodiment, the rotation of the hub (and hence the entire device) can be measured by fitting a plane to the known shape profile inside the hub, and tracking the orientation of that plane over time. In one embodiment, a model of a fenestrated endograft is rotated to better align the fenestrations on the endograft with an anatomical model.

The rotation of the hub shape about itself is used to map the rotation of the endograft that is housed within a distal portion of the device. This allows any commercial catheter (manual or robotic), deployment system, sheath, or other such device to be navigated using a shape sensed guidewire. This can be applied to many applications such as vascular (catheters, sheaths, deployment systems, etc.), endoluminal (endoscopes), orthopedic (k-wires & screwdrivers) as well as non-medical applications.

To provide a more efficient registration, a deformable registration device utilizing Fiber-Optical RealShape™ (FORS™ also known as "Optical Shape Sensing", "Fiber Shape Sensing", "Fiber Optical 3D Shape Sensing", "Fiber Optic Shape Sensing and Localization" or the like) may be employed. A Fiber-Optical RealShape™ system is a commercial name for systems developed by Koninklijke Philips, N.V. As used herein, the terms FORS™ and FORS™ systems are not, however, limited to products and systems of Koninklijke Philips, N.V., but refer generally to fiber optic shape sensing and fiber optic shape sensing systems, fiber optic 3D shape sensing, fiber optic 3D shape sensing systems, fiber optic shape sensing and localization and similar technologies.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for monitoring shape sensing enabled devices and other devices is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing module 122 configured to interpret optical feedback signals from a shape sensing device or system 104 (FORS™). Optical sensing module 122 is configured to use the optical signal feedback (and any other feedback) to reconstruct deformations, deflections and other changes associated with shape sensed devices. In accordance with the present principles, a medical device or instrument 102 includes a lumen 103, which receives a guidewire or other elongated flexible instrument 108 therein. The guidewire 108 is configured to receive the system 104 therethrough. The medical device 102 may include a catheter, a sheath, a probe, an endoscope, a robot, an electrode, a filter device, a balloon device, a graft, a stent or other medical component having a lumen, etc. The medical device 102 is considered to be an over-the-wire device or component. The medical device 102 includes a hub 106 that may be configured within the device 102, applied (connected/coupled) to the device 102 or configured to fit within the device 102.

The shape sensing system 104 includes one or more optical fibers which may be arranged in a set pattern or patterns. The optical fibers 126 connect to the workstation 112 through cabling. The cabling may include fiber optics, electrical connections, other instrumentation, etc., as needed.

System 104 with fiber optics may be based on fiber optic Bragg grating sensors, Rayleigh scattering, or other types of scattering. Inherent backscatter in conventional optical fiber can be exploited, such as Raleigh, Raman, Brillouin or fluorescence scattering. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, or in multiple single-core fibers arranged together, the 3D shape and dynamics of the surface of interest can be followed.

A fiber optic Bragg grating (FBG) system may also be employed for system 104. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Fresnel reflection at each of the interfaces where the refractive index is changing is measured. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors.

Incorporating three or more cores permits a three dimensional form of such a structure to be precisely determined. From the strain measurement, the curvature of the structure can be inferred at that position. From the multitude of measured positions, the total three-dimensional form is determined. A similar technique can be employed for multiple single-core fibers configured in a known structure or geometry.

In one embodiment, workstation 112 is configured to receive feedback from the shape sensing device 104 and record accumulated position data as to where the sensing device 104 has been within a volume 130. The shape sensing information within the space or volume 130 can be displayed on a display device 118. Workstation 112 includes the display 118 for viewing internal images of a subject (patient) or volume 130 and may include shape images 134 as an overlay on medical images 136 such as x-ray images, computed tomography (CT) images, magnetic resonance images (MRI), real-time internal video images or other images as collected by an imaging system 110 in advance or concurrently. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A registration device 144 is stored in memory 116 and is configured to register the hub 106 to a target node(s) 124 in the over-the-wire device 102. The target node 124 may include any identifying features on the device 102 that can be employed as a reference for the hub 106. The device 102 and the target node 124 are preferably visualized in an image or images 136. In addition, a virtual model 146 of the over-the-wire device 102 may be rendered using the target node 124 as a reference to visualize in the over-the-wire device 102.

In one embodiment, the hub 106 is registered to the target node 124 in the over-the-wire device 102 by attaching the hub 106 to a proximal portion of an over-the-wire device 102 to enable a registration (e.g., longitudinal) between the shape sensed guidewire 108 and the over-the-wire device 102. To create a meaningful visualization of the over-the-wire device 102, the hub location may be mapped to other device nodes. Nodes 124 are considered to be device features of interest to the clinician. Examples may include a device tip, a position of a fenestration, start and end points of a balloon, location of an ultrasound transducer, etc.

In one embodiment, the target node 124 may include a tip position of the device 102. This node may be employed for positioning many devices and may be employed for safety reasons (e.g., making sure that the tip does not protrude too far into certain vessels and that the tip of the device remains inside the vessel, etc.). When the hub 106 is attached to the over-the-wire device 102, it is not possible to correctly visualize the device 102 in space until the mapping between the tip of the device 102 and the hub 106 is known.

This mapping can be done in a plurality of ways. For example, a length of the device 102 may be input to an image processing module 148, which renders a position and dimension(s) of the devices using visualization software. This may be provided by scanning a barcode of the device 102 and looking up its properties in a database, the user entering a value directly or reading values from a device package, measuring by hand, etc. In another embodiment, the device 102 may be recognized by the image processing module 148 using an x-ray image and automatically looking up the information from a database. This would be difficult for non-distinct devices, such as navigational catheters, but is easier for endografts and more complex devices. In another embodiment, the device 102 may be placed and attached to the hub 106 in an x-ray field of view (FOV) and have its length/dimension automatically detected from the resulting image. This may be challenging for some devices (102); however, navigation catheters could be coiled up to fit within the FOV.

Figure 2:
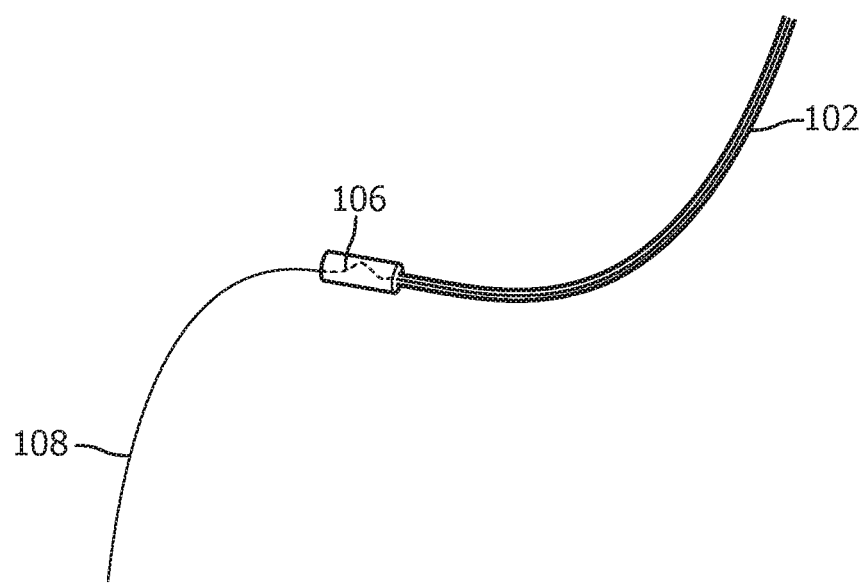
FIG. 2 is a schematic diagram showing distal end registration in accordance with one embodiment.

Referring to FIG. 2, a technique for aligning and registering a tip of an over-the-wire device 102 with a hub 106 is illustratively shown. Alignment of the guidewire 108 and device 102 (e.g., catheter) includes aligning a distal tip of the guidewire 108 with the device 102 to measure the length of the over-the-wire device 102. Once manually aligned, a measurement may be initiated by optical sensing module 122 (FIG. 1) to measure a dimension of device 102.

Figure 3:
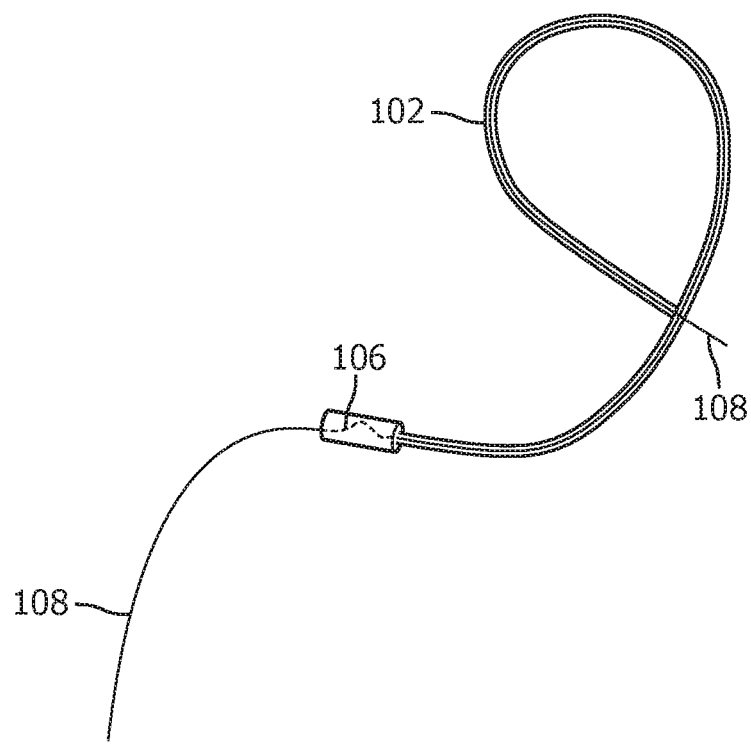
FIG. 3 is a schematic diagram showing registration of a tip and length which includes a loop-back of a catheter tip in accordance with one embodiment.

Referring to FIG. 3, registration of the tip and length of device 102 may include a loop-back of a catheter tip. Here, the guidewire 108 fully extends through the over-the-wire device 102. The device 102 (e.g., catheter) is looped back so that its tip is touching a more proximal part of itself. Once manually aligned, a measurement may be initiated by optical sensing module 122 (FIG. 1) to measure a dimension of device 102.

Figure 4:
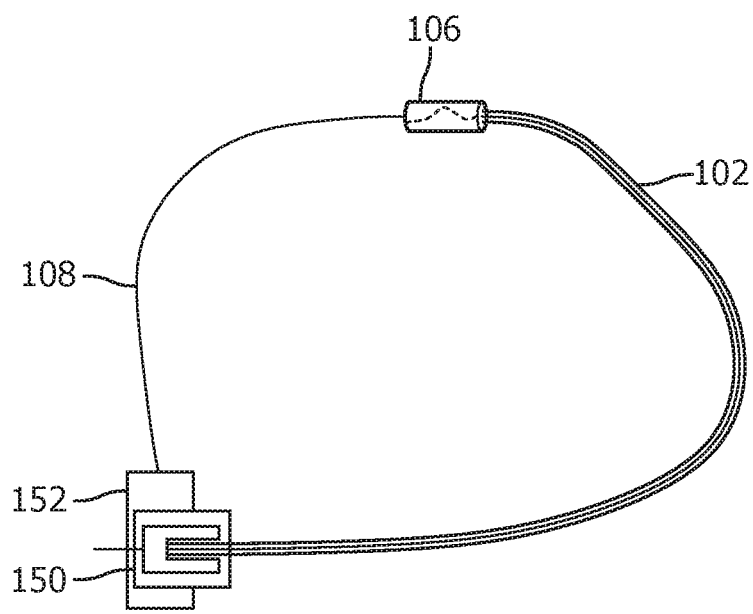
FIG. 4 is a schematic diagram showing registration using a registration fixture in accordance with one embodiment.

Referring to FIG. 4, an example of registration of a tip and length the device 102 is shown by employing a measurement fixture 150 that is co-located with a launch fixture 152 for the FORS™ system 104 (FIG. 1). In this embodiment, the guidewire 108 fully extends through the over-the-wire device 102. The over-the-wire device 102 is inserted into the measurement fixture 150 that has a known position with respect to the guidewire 108. The position of the tip of the device 102 (e.g., catheter) is computed. The measurement fixture/feature 150 may be integrated into the launch fixture or launch base of the shape sensed guidewire 108.

The described techniques are suitable for identifying the tip of the device 102. In many situations, for example, with navigation catheters, this information sufficiently captures the necessary information to display a clinically meaningful visualization of the device 102 to the operator. However, there are many devices where the length of the device does not fully capture the clinically-relevant nodes. These devices include, e.g., balloon catheters, endograft deployment systems, valve deployment systems, mitral clip deployment systems, stent catheters, imaging and measurement catheters (intracoronary temperature (ICT), intravascular ultrasound (IVUS), fractional flow reserve (FFR) measurements, etc.) amongst others. In such cases, the tip position is useful, but the other feature/node positions on the over-the-wire device 102 may have higher importance. For example, in endograft deployment for EVAR, a deployment device is navigated over a guidewire and aligned in the aorta. A retaining ring of the endograft needs to be positioned such that it does not block the bifurcations to the renal arteries. In other cases where the endograft has fenestrations, it may also need to be rotated so that the fenestrations align correctly with the branching vessels. In this example, the tip of the deployment system is only relevant in terms of safety—it does not include any relevant information about the position and orientation of the endograft itself. As such, a secondary or different registration becomes relevant, e.g., the registration between the hub 106 and clinically relevant nodes (124).

There are multiple ways to perform this registration. In one example, a location of the node (124) may be directly input to visualization software (image processing module 148, FIG. 1). This may be suitable for certain devices where the nodes are very reproducible (balloon catheters). In other devices, such as endografts, there may not be a controlled position of the endograft in every device. In another example, a position of the device under x-ray may be employed. The nodes (124) may be denoted with a radio-opaque markers. The radio-opaque markers can be manually identified by the clinician, can be automatically identified, or a combination of the two. The shape sensed guidewire needs to be registered to the x-ray image. The nearest shape node to the x-ray (x, y) position can be employed as the relevant node (124). This can be done prior to or during the procedure. In yet another example, alternative intra-operative imaging modalities may be employed. There modalities may include, e.g., computed tomography (CT), magnetic resonance imaging (MRI), ultrasound, etc., instead of x-ray. Registration can also be performed to measure the width of the device 102, or other relevant features.

Figure 5:
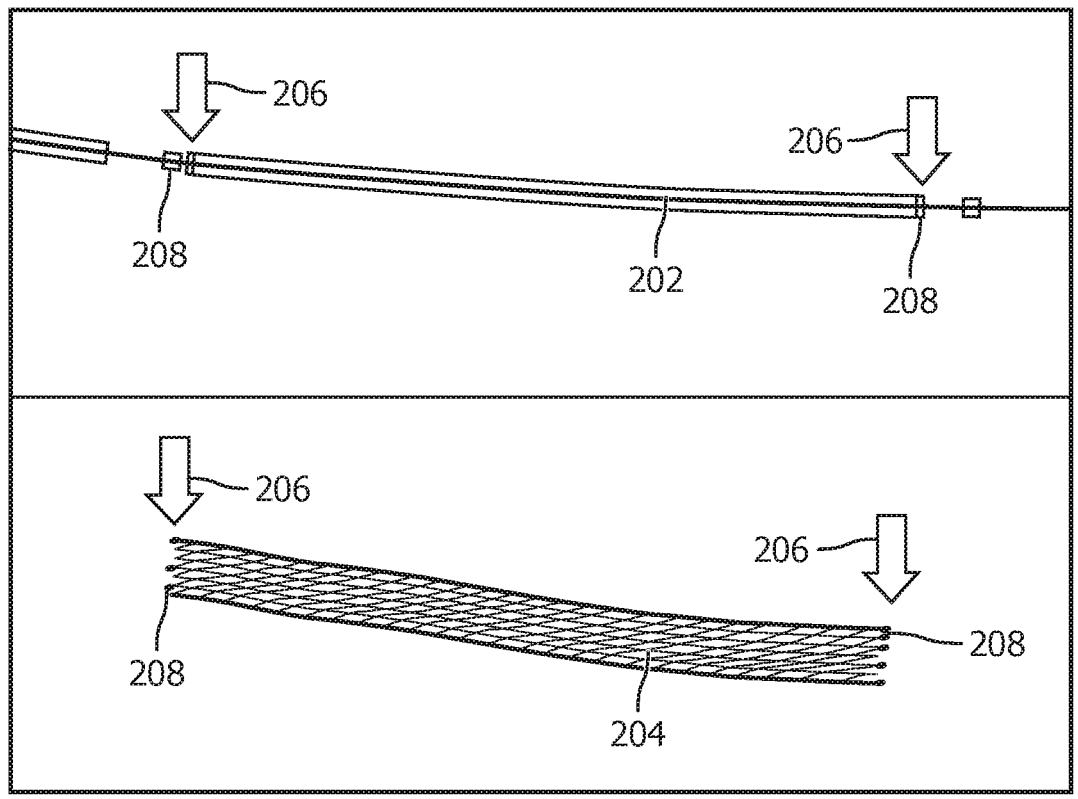
FIG. 5 shows images of an undeployed stent and a deployed stent with radiopaque markers for registration in accordance with an illustrative embodiment.

Referring to FIG. 5, an undeployed stent 202 and a deployed stent 204 are shown with arrows 206 indicating (radiopaque) markers 208 that can be used to identify the relevant nodes (e.g., node 124 in FIG. 1) on the over-the-wire device 102 (FIG. 1) in accordance with one embodiment.

Figure 6:
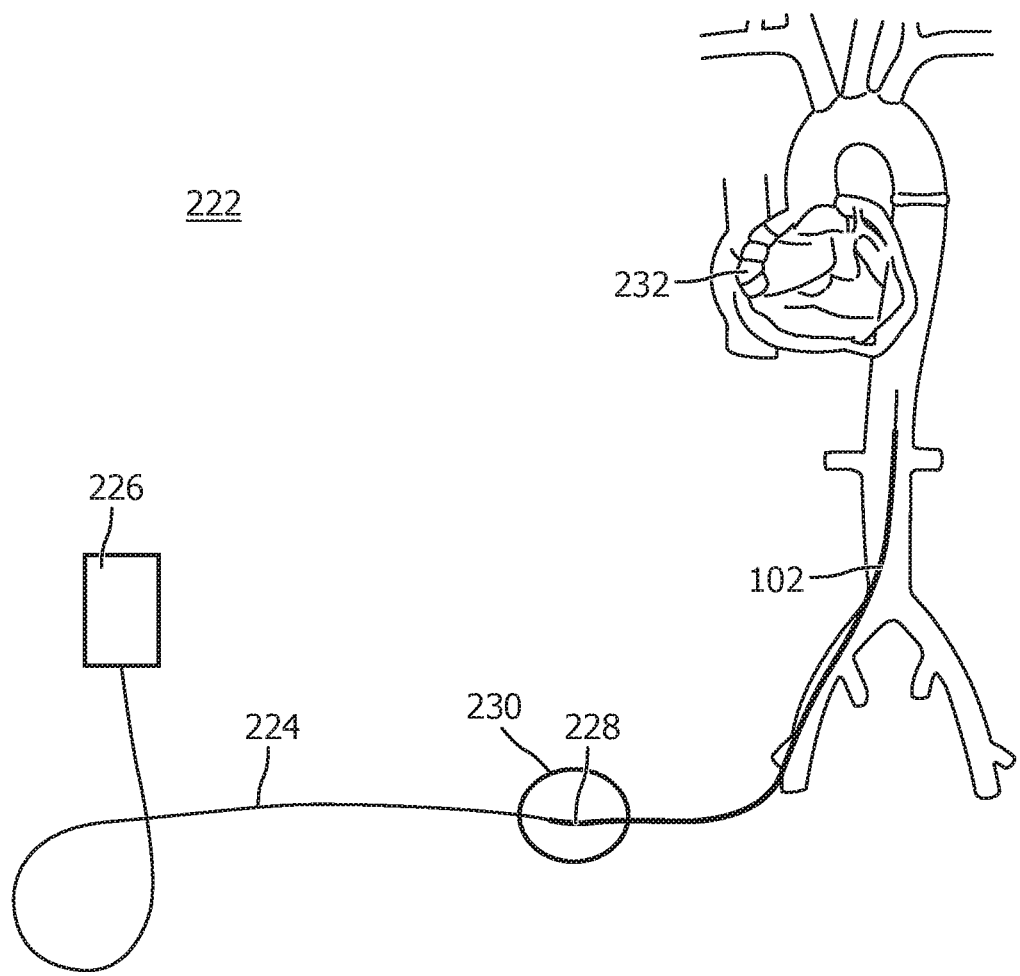
FIG. 6 is a virtual image showing a visualization of an over-the-wire device showing a length of the device in a specific color and thickness overlaid on an imaging model diagram in accordance with one embodiment.

Referring to FIG. 6, the over-the-wire device 102 can be visualized using a FORS™ system. Visualization of the over-the-wire device 102 can be done by showing a length of the device in a specific color and thickness overlaid on an imaging model, e.g., of a blood vessel/heart 232. A sample image 222 of a shape-sensed guidewire 224 exiting a launch fixture 226 and then passing through a hub curvature 228 is illustratively depicted. A catheter 102 is shown as a thicker line than the guidewire 224 and extends from the start of a hub 230 to its known length. The guidewire 224 extends slightly beyond the tip of the catheter 102. Each component may be depicted in a different color or texture to provide visualization of the catheter 102 on the display 118 (FIG. 1). A model of the hub 230 (circled) can also be shown along the catheter 102 to give the operator a frame of reference.

Figure 7:
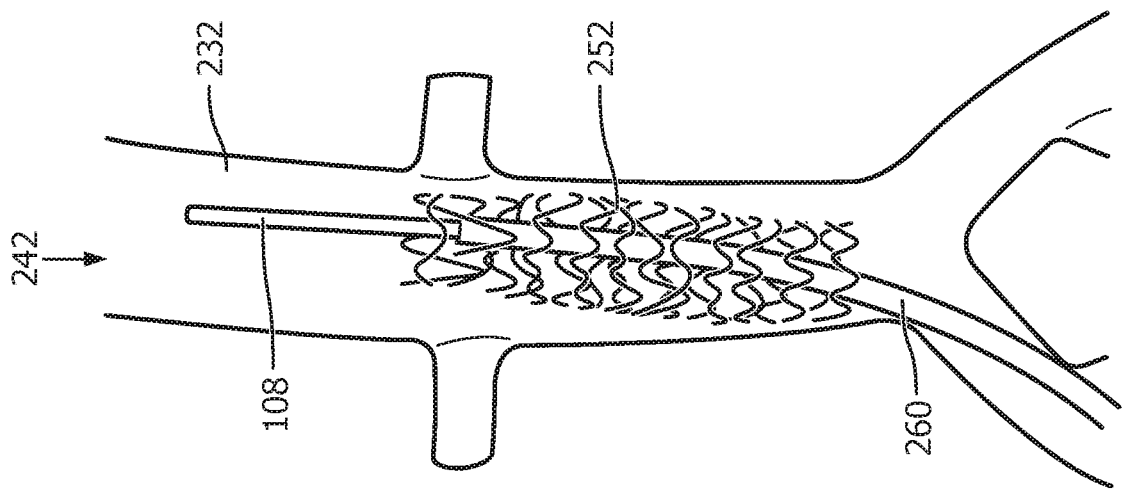
FIG. 7 is a virtual image showing a visualization of an over-the-wire device feature model and physical model in accordance with one embodiment.
Figure 7:
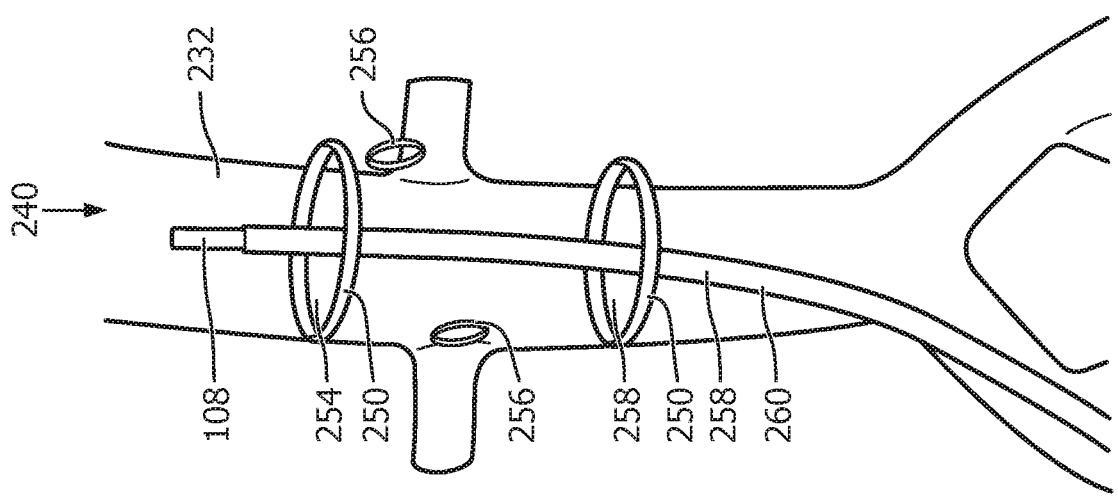

Referring to FIG. 7, virtual representations of an endograft are illustratively shown. A position and orientation of a model 250, 252 is tied to a target node (not shown) along an over-the-wire deployment system. Its position and orientation are known by using a hub with a shape sensed guidewire 108. Once target nodes are registered and identified, they can be displayed to the user to give the user guidance during positioning of the over-the-wire device represented as model 250, 252. FIG. 7 shows two instances. Instance 240 shows a feature model 250, and instance 242 shows a physical model 252 of the endograft. The model 250 shows relevant features of the endograft such as the location of a top retaining ring 254, fenestrations 256 and an end/bottom 258 of the endograft. The physical model 252 of the deployed endograft is visualized, allowing the doctor to see what position the endograft would take up if the deployment were performed in that position and orientation. The position and orientation of the model 250, 252 is mapped to any relevant and selected target node on a virtual catheter 260, as determined during a registration step.

Figure 8:
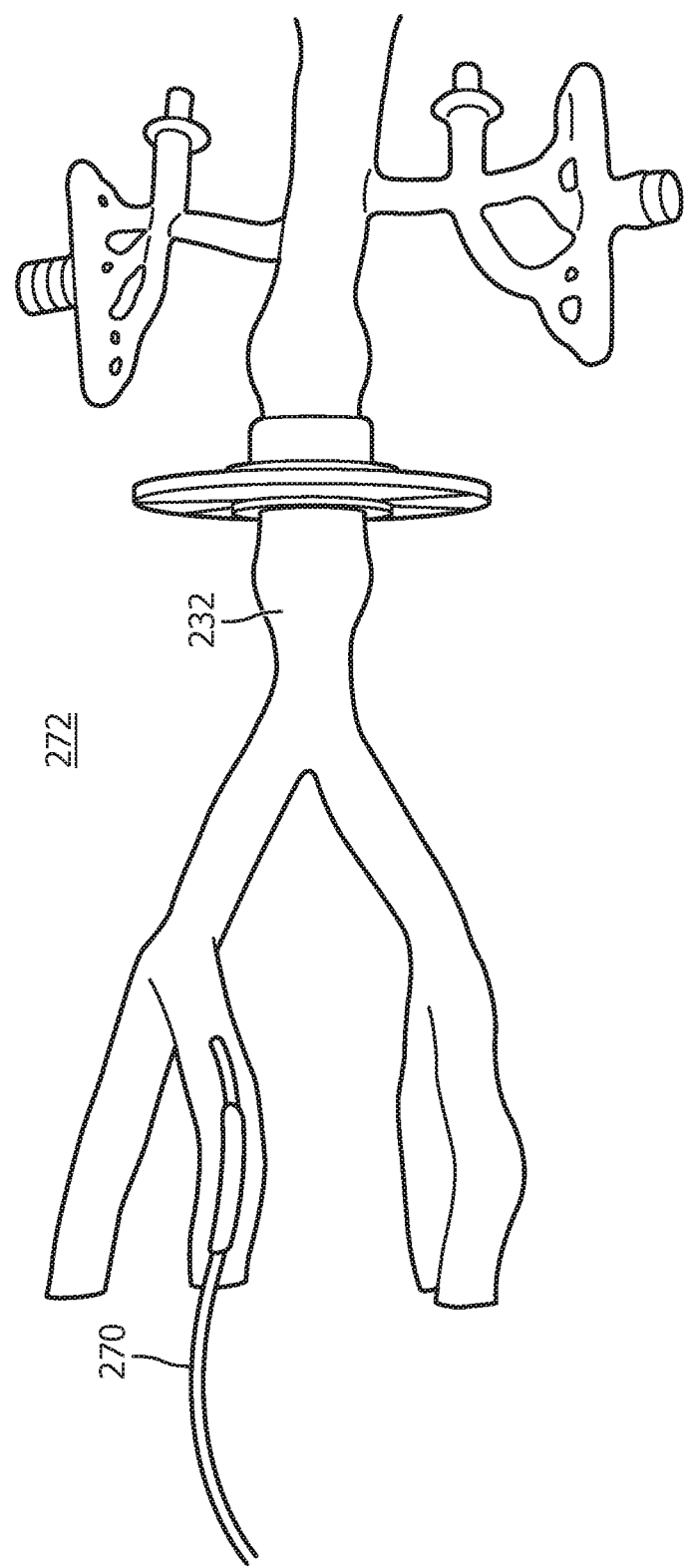
FIG. 8 is a virtual image showing a visualization of an over-the-wire device as a balloon where the balloon includes a plurality of nodes to map expansion in accordance with one embodiment.

Referring to FIG. 8, a virtual representation of a balloon catheter 270 is illustratively shown in a blood vessel 272 in accordance with another example. A balloon position is tied to a target node along the over-the-wire deployment system. The position is known by using a hub with a shape sensed guidewire. A model of balloon catheter 270 is not mapped to a single shape node, but rather a series of shape nodes along the fiber. This permits the model, in this case the balloon, to be deformed according to the current shape of the device.

The models that are described for device visualization can take on many forms. These may include a predicted model of the device that may include relevant features such as anchor points, fenestrations, or the location of radio-opaque markers. A model of the device may be taken from a database where the selected model can be adjusted by the user (undeployed, partially deployed, fully deployed, etc.). A 2D or 3D representation of the device as generated by the intraoperative imaging (e.g., fluoroscopy, XPER CT™, bi-plane fluoroscopy, ultrasound, etc.). The model can be updated using the live anatomical imaging at any time that it is available. While the present principles have been described using devices that run over shape sensed guidewires, the present principles are not limited to a guidewire as the shape sensed device. It can be stated more broadly as any tool with a shape sensed fiber within it that is used to infer shape of another tool. The use of an attachable hub is provided to cause the shape deformation of a shape sensed guidewire or tool through the visual shape representation of a device that is not enabled with shape sensing but that is being used with the shape sensed tool. This permits any commercial catheter (manual or robotic), deployment system, sheath, or other such device to be navigated using a shape sensed guidewire (or other tool). This may be applied to a plurality of useful applications, such as, e.g., vascular (catheters, sheaths, deployment systems, etc.), endoluminal (endoscopes), orthopedic (k-wires and screwdrivers) as well as non-medical applications and also applies to both manual and robotic manipulation of such devices.

Figure 9:
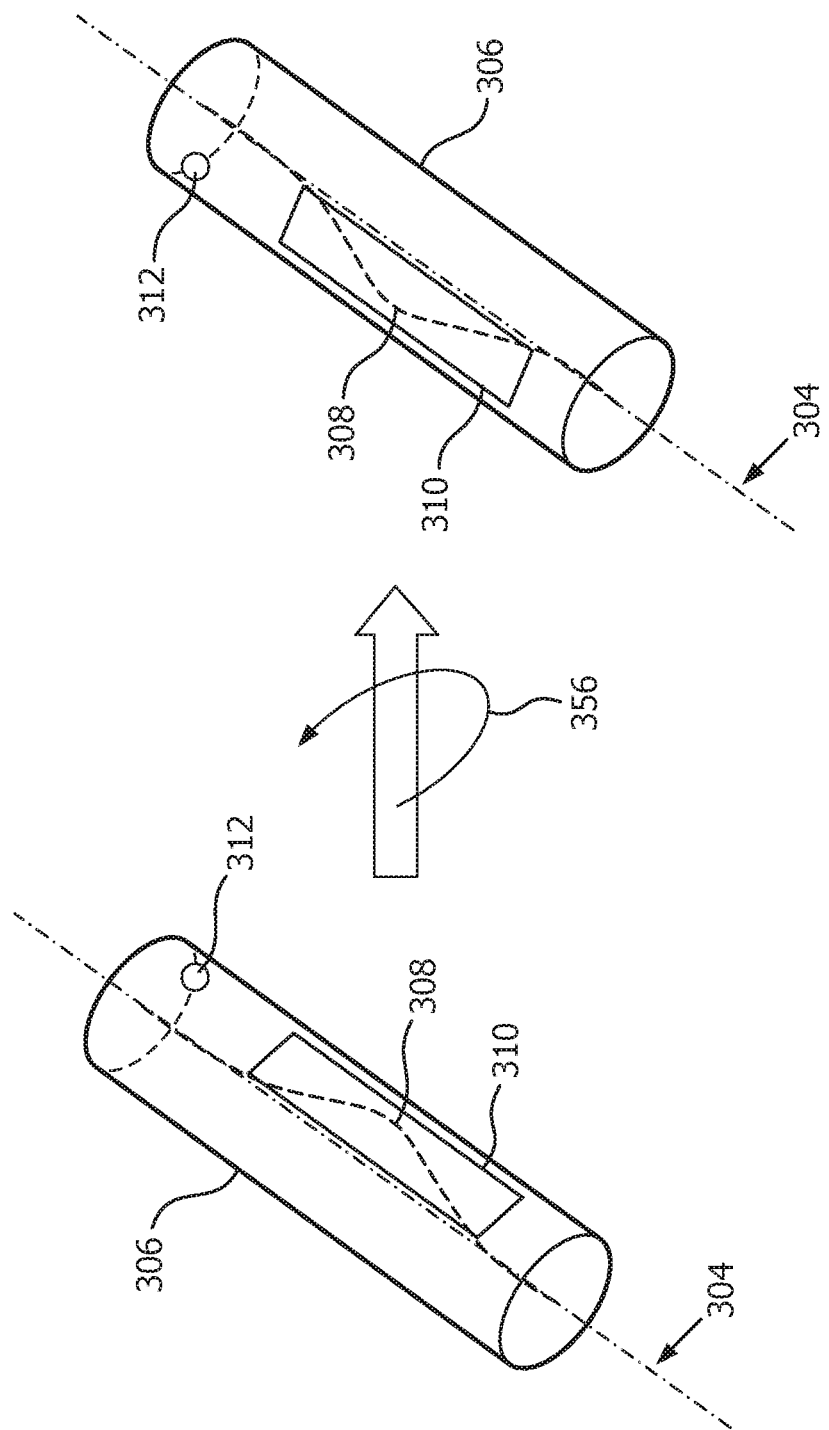
FIG. 9 is a schematic diagram showing a rotation of an over-the-wire device for tracking using a plane defined by a hub in accordance with one embodiment.

Referring to FIG. 9, a proximal hub attachment 306 is shown for determining an orientation of a distal portion of a device (not shown). The hub 306 includes a shape profile 308 that deflects a shape-sensed guidewire 304 passing through it into a known shape. That shape can be detected along an optical fiber of the shape-sensed guidewire 304 to determine a longitudinal registration between the guidewire 304 and an over-the-wire device such as a catheter, endograft deployment system, etc., which may be coupled to the hub 306. Since the hub 306 is coupled to the over-the-wire device, the hub shape can also be used to track the rotation applied to a proximal part of the over-the-wire device.

In one embodiment, the rotation of the hub 306 (and hence the entire device) can be measured by fitting a plane 310 to the known shape profile 308 inside the hub 306, and tracking the orientation of that plane 310 over time. The shape profile 308 may include a 2D or 3D shape that preferably is off-axis relative to to longitudinal axis. A visual reference point 312 may be employed for visualization in images and/or locating the hub 306 relative to the over-the-wire device.

Figure 10:
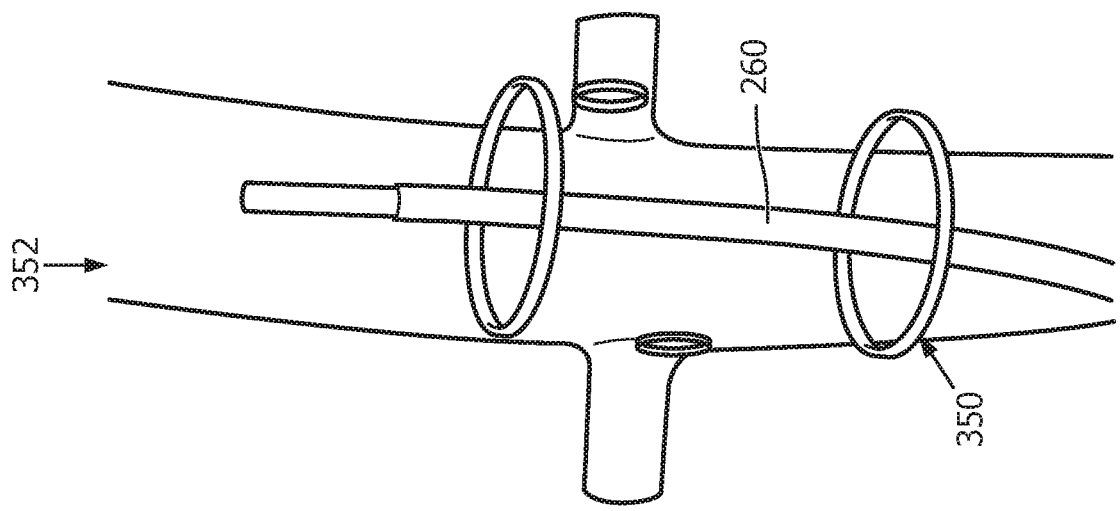
FIG. 10 is a schematic diagram showing a virtual model corresponding with the rotation of FIG. 9 for the over-the-wire device in accordance with one embodiment.
Figure 10:
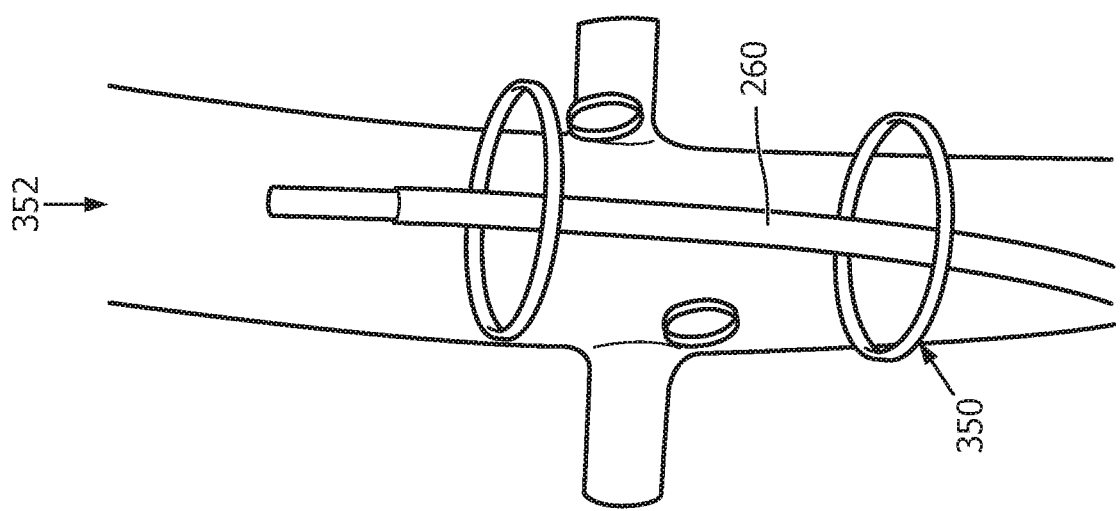

Referring to FIG. 10, a model 350 of a fenestrated endograft is being rotated to better align the fenestrations on the endograft with an anatomical model 352. The rotation of the hub shape about itself is used to map the rotation of the endograft model 350, which includes the hub 306 within a distal portion.

Referring to FIGS. 9 and 10, the orientation of the distal virtual model 350 in FIG. 10 follows a counter-clockwise rotation 356 of the hub 306 shown in FIG. 9. The same counter-clockwise rotation of the hub 306 can be measured by fitting the plane 310 to the known shape and tracking the orientation of the plane 310 over time. In an alternative embodiment, the shape within the hub 306 is in three dimensions and not planar as depicted in FIG. 9. In such an embodiment, the orientation of the 3D shape would be tracked over time with registration techniques that are known in the art.

The torque properties of the over-the-wire device (endograft, etc.) can be employed to map the torqueing of the hub 306 to torqueing of a distal node or portion of the device. In many therapeutic devices such as endograft deployment systems, this will be a nearly 1-to-1 relationship. In other devices such as navigation catheters, this may not be a 1-to-1 relationship and the torque properties will depend heavily on the shape of the device and the properties of the devices. In such a situation, a model can be used to predict the expected orientation in the proximal section by using the known information of the device shape, hub orientation, and device properties.

Imaging can be used to complement this technique. An initial registration between the orientation of the proximal part of the device and the orientation of the hub can be performed using image-based registration using x-ray, ultrasound, CT, MRI, etc. Periodic imaging of the distal part of the device can be used to update the model or the predicted orientation of the device. One or multiple projections may be used. User input can also be used to update the predicted orientation. Alternatively, the hub 306 may attach to the device in a repeatable manner so that the registration is already known as soon as the hub 306 is attached.

In complex anatomies, it may be challenging for the user to mentally map the proximal hub rotation direction to the distal rotation desired. In one embodiment, the user can place targets on a model of the anatomy (for example, generated through pre-operative or intra-operative imaging). These targets are mapped to specific features of the device to be deployed or oriented. The visualization software of the image processing module 148 (FIG. 1) can determine the rotational angle between the current position of the device and the target position of the device and then inform the user how far and in which direction to rotate the hub 306. This calculation could also account for the known torque mapping in cases where it is not 1-to-1. This feature may be especially useful in steerable and robotic catheters that have a need for instinctive driving.

Figure 11:
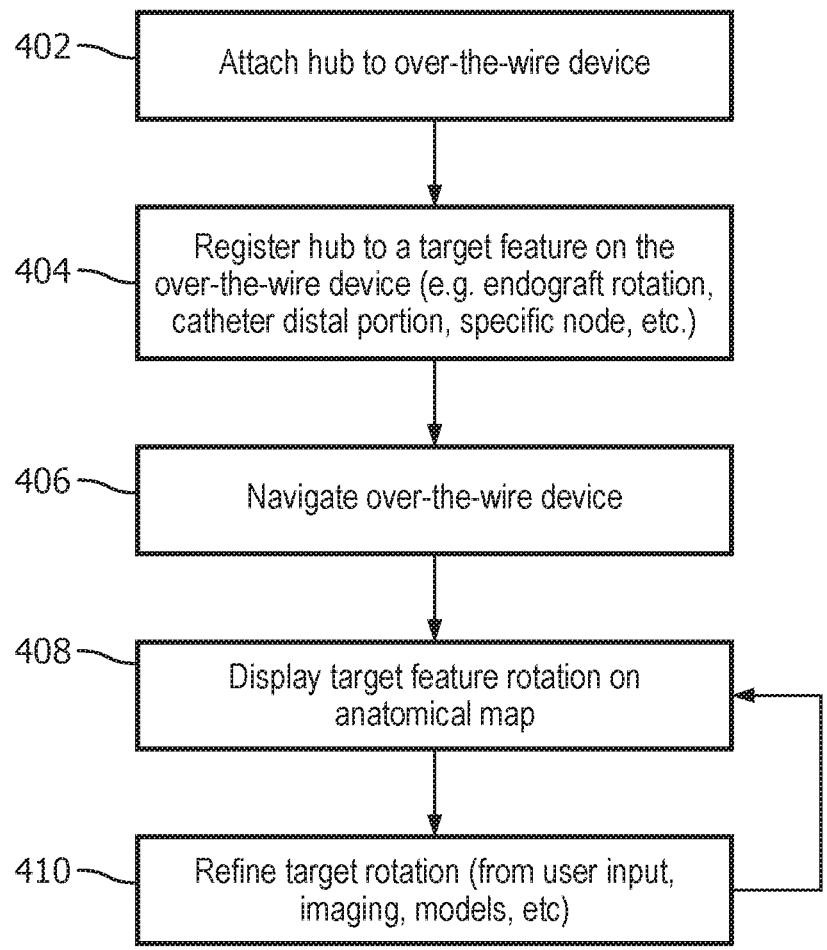
FIG. 11 is a block/flow diagram showing a method for deploying an instrument using a hub for tracking in accordance with one embodiment.

Referring to FIG. 11, a block/flow diagram shows a workflow for using orientation from a hub during over-the-wire device deployment in accordance with one embodiment. In block 402, the hub is attached to the over-the-wire device. The hub may connect directly to the over-the-wire device or be integrally formed in the over-the-wire device. The hub should translate and rotate along with the over-the-wire device. In one embodiment, when employing a Luer-lock type hub, the hub may have an additional feature to couple to the over-the-wire device in a torsionally stiff manner, thus avoiding loosening the Luer connection when such an action is not desired.

In block 404, the hub orientation is registered to a target feature (or features) on the over-the-wire device. A reference point or feature on the hub is matched up with or aligned with a node or feature on the over-the-wire device. This may include different physical features for different over-the-wire devices. For example, a passive feature that can be added to assist with the rotational alignment of the over-the-wire device using the hub may include a dot or raised groove on the hub to identify a unique rotational position. The features may include or be associated with, e.g., endograft rotation, catheter distal portion, a specific node along the distal portion, etc.

In block 406, the over-the-wire device is navigated over a shape sensed guidewire. The shape sensed guidewire or other tool passes through the hub and is shaped by the hub. The hub in turn is coupled to the over-the-wire device. In block 408, a motion of a target feature is displayed on an anatomical map. In block 408, the target feature's position is refined using user input, the imaging (e.g., intraoperative imaging), using models, etc. The path loops back to block 406 until a desired position is achieved for the over-the-wire device. For non-therapeutic measurement devices, a known orientation at the time of measurement can assist to stitch rotational images or measurements together.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for a hub for device orientation with an optical shape sensed guidewire (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for deploying a device, comprising:
an elongated flexible instrument comprising a shape-sensed guidewire;
a shape sensing system disposed within the shape-sensed guidewire, the shape sensing system being coupled to the flexible instrument;
a deployable device; and
a hub having a shape profile that deflects the shape-sensed guidewire passing through it into a known shape, the shape profile being configured to: longitudinally receive and maintain the elongated flexible instrument with the shape sensing system therein; and track at least one of a position or a rotation of the hub relative to a reference position using the shape sensing system, wherein the hub is configured to be longitudinally coupled to a proximal portion of the deployable device such that a change in the at least one of position or rotation of the hub indicates a corresponding change in the deployable device.

2. The system as recited in claim 1, wherein the shape profile includes a two-dimensional or three-dimensional off-axis shape or strain.

3. The system as recited in claim 1, wherein the deployable device includes one of a catheter, a sheath, a balloon or an implantable device and the hub connects to the deployable device.

4. The system as recited in claim 1, wherein the reference position includes an anatomical feature.

5. The system as recited in claim 1, further comprising a registration module to register the hub with the deployable device to track the changes in the hub with the deployable device.

6. The system as recited in claim 1, further comprising a display to depict a representation of the deployable device in accordance with the hub.

7. The system as recited in claim 1, further comprising an image processing module configured to render images of the deployable device or a model thereof in accordance with shape data from the hub.

8. A system for deploying a device, comprising:
a shape sense enabled guidewire;
a hub having a shape profile that deflects the shape sense enabled guidewire passing through it into a known shape, the shape profile configured to longitudinally receive and maintain the shape sense enabled guidewire therein, wherein the shape profile comprises a shape to permit identification of at least one of a position or a rotation of the hub relative to a reference position using shape sensing;
an over-the-wire device having a proximal portion longitudinally connectable to the hub during a deployment of the device over the guidewire; and
a registration module to register anatomical images with the hub to infer a position or rotation of the over-the-wire device in accordance with the at least one of position or rotation of the hub.

9. The system as recited in claim 8, further comprising a shape sensing system disposed within the guidewire.

10. The system as recited in claim 8, wherein the shape profile includes a two-dimensional or three-dimensional off-axis shape.

11. The system as recited in claim 8, wherein the over-the-wire device includes one of a catheter, a sheath, a balloon or an implantable device.

12. The system as recited in claim 8, wherein the reference position includes an anatomical feature.

13. The system as recited in claim 8, further comprising an image processing module configured to render images of the device or a model thereof in accordance with shape data from the hub.

14. The system as recited in claim 8, further comprising a display to depict a representation of the device in accordance with the hub.

15. A system for deploying a device, comprising:
an elongated flexible instrument;
a shape sensing system coupled to the elongated flexible instrument;
a deployable device comprising one of a catheter, a sheath, a balloon or an implantable device; and
a hub, which connects to the deployable device, and comprising a profile having a shape profile that deflects the shape sense enabled guidewire passing through it into a known shape, the shape profile being configured to longitudinally receive and maintain the elongated flexible instrument with the shape sensing system therein, wherein: the hub is configured to be longitudinally coupled to a proximal portion of the deployable device such that a change in at least one of position or rotation of the hub indicates a corresponding change in the deployable device; the profile is configured to track at least one of a position or a rotation of the hub relative to a reference position using the shape sensing system; and the hub is configured to be longitudinally coupled to a proximal portion of a deployable device such that a change in the at least one of position or rotation of the hub indicates a corresponding change in the deployable device.

16. The system as recited in claim 15, wherein the profile includes a two-dimensional or three-dimensional off-axis shape or strain.

17. The system as recited in claim 15, wherein the reference position includes an anatomical feature.

18. The system as recited in claim 15, further comprising a registration module to register the hub with the deployable device to track the changes in the hub with the deployable device.

19. The system as recited in claim 15, further comprising a display to depict a representation of the deployable device in accordance with the hub.

\* \* \* \* \*